Figure 1:
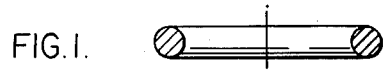

United States Patent [19]

Suovaniemi et al.

[11] 4,147,752
[45] Apr. 3, 1979

[54] FORM PIECE FOR APPARATUSES USED FOR IMMUNOASSAYS AND ENZYME REACTIONS

[75] Inventors: Osmo A. Suovaniemi; Pertti Ekholm; Jukka Suni; Johan Järnefelt, all of Helsinki, Finland

[73] Assignee: Kommandiittihytio Finnpipette Osmo A. Souvaniemi, Helsinki, Finland

[21] Appl. No.: 868,491

[22] Filed: Jan. 11, 1978

[30] Foreign Application Priority Data

Jan. 14, 1977 [FI] Finland .................................. 770116

[51] Int. Cl.² .......................................... G01N 33/16
[52] U.S. Cl. ............................. 422/57; 195/103.5 A; 195/127; 23/230 B; 23/915; 23/920
[58] Field of Search ............... 23/253 TP, 259, 230 B; 424/1, 12, 16; 195/103.5 A, 127

[56] References Cited

U.S. PATENT DOCUMENTS

| 3,646,346 | 2/1972 | Catt | 23/230 B |
|---|---|---|---|
| 3,770,383 | 11/1973 | Price | 23/253 TP |
| 3,810,739 | 5/1974 | Nussbaum | 23/253 TP |
| 3,826,619 | 7/1974 | Bratu, Jr. et al. | 23/259 X |
| 3,854,883 | 12/1974 | Montagnon | 23/253 TP |
| 3,876,378 | 4/1975 | Montagnon | 23/253 TP |
| 4,054,646 | 10/1977 | Giaver | 23/253 TP |

Primary Examiner—R. E. Serwin
Attorney, Agent, or Firm—Hopgood, Calimafde, Kalil, Blaustein & Lieberman

[57] ABSTRACT

A form piece is disclosed which may be mounted in a test tube cuvette or similar vessel and is coated with an antibody, enzyme or other material to be used in laboratory tests. The form piece is preferably made in a ring-like configuration and includes projecting members which space the form piece from the sides of the vessel.

8 Claims, 15 Drawing Figures

U.S. Patent  Apr. 3, 1979  Sheet 2 of 3  4,147,752

FORM PIECE FOR APPARATUSES USED FOR IMMUNOASSAYS AND ENZYME REACTIONS

The subject of the present invention is a form piece for apparatuses used for immunoassays and enzyme reactions, which form piece increases the accuracy, reproducibility, and convenience and speed of determination and which apparatus includes a form piece that can be placed into a test tube, cuvette, or similar vessel and that is coated with an antibody, enzyme or with a protein of another type, with an antigen or haptene, such as carbohydrate.

The form piece subject of the invention may be employed in immunoassays, such as radioimmunoassay (RIA), enzyme immunoassay (EIA), enzyme-linked immunosorbent assay (ELISA), haemagglutination inhibition (HI), viroimmunoassay, fluoroimmunoassay, and spinimmunoassay. It is furthermore appropriate to be used in techniques and methods wherein immobilized enzymes are used, either as such or combined with other procedures.

Radioimmunoassay methods, among others, are being superseded, e.g., by enzyme immunoassays (EIA, ELISA and EMIT) because these are mostly specific and sensitive enough in many determinations. The equipment needed in them is relatively inexpensive and mostly already in existence in laboratories, the reagents are inexpensive and have a long shelf life, the treatments are simple, the determinations are fast, and they afford possibilities of automation; no isotopes and no isotope counters are needed.

EIA, ELISA and EMIT are appropriate for use in determining antigens, antibodies and haptenes.

Enzymes, such as alkaline phosphatase, peroxydase, glucose oxidase, glucose-6-phosphate hydrogenase, etc., are used as markers. The antigen, antibody or haptene enzyme conjugate required in these assays is stable and has a long shelf life.

All types of EIA (ELISA) (competitive EIA for antigen, immunoenzymometric assay for antigen, sandwich EIA for antigen, EIA for antibody) excepting homogeneous EIA (EMIT), imply a method by which the bound or free conjugate may be separated.

Among others, in the separation the so-called solid phase is employed to which the antigen or antibody is fixed:

1. Adsorption to the surface of a plastic or glass tube
2. Covalent linkage e.g. with dextrane, polyacrylamide, agarose, cellulose, polystyrene.

As a rule, the method by which the antigen or antibody is fixed to the solid phase is the following:

A given quantity of antigen or antibody solution is pipetted, e.g., into a plastic tube, where the inner tube surface contacted by the fluid becomes coated with antigens or antibodies. This procedure has several drawbacks:

1. The method is inaccurate in that the quantity of said protein adhering to the inner tube surface varies from tube to tube, e.g., owing to the fact that the inner surface area of the tube contacted by the fluid varies.
2. The material of which the tubes are made is not always the best possible material in view of protein fixation.
3. For the cuvettes, which have to be transparent, only certain materials may be chosen (for instance, polystyrene and acrylics). To these materials proteins can mostly be made adherent by adsorption only, whereby the optical quality is not impaired.
4. The coating of the tubes and cells with antibodies, antigens or other proteins is cumbersome in practice because it is necessary to pipette an exact amount of the protein solution into each.
5. The tubes and cuvettes require a lot of space in the coating, storage and transporting phases.
6. The tubes and cuvettes in use at present may only be stored in coated condition for a limited period. The coating has to be applied in the end user's laboratory. Hereby the laboratory work is made quite awkward since coated tubes or cuvettes are not commercially available.
7. The coated tubes and cuvettes are usually discarded after one use, and this causes high material losses.

The immobilized enzymes techniques are encumbered by the same drawbacks as have been described above. In the immobilisation of enzymes a suitable method may be used, numerous such being known in prior art.

Thus, it is understood that the enzyme assays and immunoassays for use in association with existing apparatus and equipment still require major improvement.

An antigen, antibody, haptene, enzyme or another protein or carbohydrate may be attached to a ring. The mode of attachment may be, e.g., adsorption, covalent linkage either directly or by the aid of a mediator substance to the surface of the ring, or another suitable mode of attachment. The ring material may be selected in view of the special requirements of each method: e.g., glass, cellulose or plastics. The rings may be manufactured, e.g., by cutting, compressing, stamping, pressing from thermosetting plastics, or die-casting.

In the photometer operating according to the vertical measurement principle (Finnpipette Analyzer), wherein the measuring beam travels vertically (parallelling the vertical axis of the cuvette), a protein coated ring would be proper for use. After the ring has been placed on the bottom of the cuvette, the measuring beam can pass through the lumen of the ring. The same principle may be applied and the ring employed in the depressions of a receptacle plate (Microtiter, Titertek, Meda, Cook, etc.).

The form piece in accordance with the invention is mainly characterized in that said piece has the form of a ring or of an open ring or can be brought into such a form when used and that between the outer face of said piece and the inner surface of the test tube, cuvette or corresponding vessel, means are arranged to keep said surfaces from contact with each other, means such as projections, nodules or flanges projecting from the piece concerned or from the inner surface of the test tube, cuvette or corresponding vessel, whereby the liquid or reaction mixture in the test tube, cuvette or corresponding vessel can reach contact with all faces of the piece coated with antibody, enzyme or another type of protein, antigen, or haptene, such as carbohydrate, and whereby, when the liquid or the reaction mixture is analysed, the beam of the measurement light can be passed through the centre space of the piece of the shape of a ring or open ring.

The subject of the present invention eliminates some of the above drawbacks and deficiencies. A ring appropriate in each particular method and which can be accommodated in the tube, depression, tube element or cuvette element is made of a suitable material in an appropriate shape and size. This ring may be coated, e.g., with antigen, antibody or enzyme. The coated ring may be placed in a test tube, cuvette or cuvette element (Finnpipette cuvette element ) or in a receptacle plate (Microtiter, Titertek, Meda, Cook, etc.).

A number of advantages are gained by using the ring in accordance with the invention:

1. The surface area of the ring is invariable from ring to ring, whereby the accuracy of the method increases.

2. The ring can be made in different sizes, and its surface area may be increased, e.g., by making the ring grooved or porous.

3. The material for the ring can be selected from the material which is most appropriate in the particular procedure.

4. The ring need not consist of transparent material because the light passes through the lumen of the ring (in a cuvette element or a receptacle plate).

5. It is easy to coat the rings even in large numbers so that a standard amount of protein adheres to each ring.

6. The rings require little space and their coating, storage and transport are convenient.

7. A ring to which the protein adheres by a firm bond (e.g., a covalent linkage) keeps for prolonged periods in protein-coated condition.

8. The coated rings are suitable for commercial purposes.

9. The rawmaterial waste incurred with the disposable rings is minimal.

10. The enzyme-coated rings may be used several times over. They are easy to wash and store.

11. In connection with cuvette elements or receptacle plates, either single rings may be used, or several rings simultaneously. For simultaneous use the rings may preferably be attached to a common support or transporting plate.

12. It is possible to fix one or several proteins on the rings. The ring may then consist of one or several materials, or the ring is laminated of several different materials.

13. The stability of the proteins bound to the ring most often increases. For instance, if in the case of enzymes the thermal stability increases, higher reaction temperatures may be employed, whereby the reaction rate also increases.

14. The coated rings are excellently suited for use in association with Finnpipette cuvette elements and receptacle plates. The Finnpipette cuvette element is evaluated in a photometer with vertical passage of the light, in the direction of the longitudinal cuvette axis. The receptacle plates are also evaluated in vertical direction, which implies that in them, too, the light must be able to pass through the bottom of the depression, in the direction of the vertical cell axis. The ring is usable with all types of receptacle plates (those with level, V-shaped and U-shaped bottom).

The ring may be so constructed that within it there is space for a protein either in free condition, affixed to a suitable material, or on the inner surface of the ring. The wall of such a ring has apertures from the interior space to the outer surface of the ring, and these apertures are preferentially so small that the protein, or another large molecule, cannot pass through them. A ring of this kind may also serve, e.g., as an enzyme electrode.

Another special embodiment is a body which has been coated with protein and is connected by a stem to a cork stopper or to a supporting plate. The supporting plate carries a plurality of such bodies with stem. The stem enables, if required, e.g., the position of the body in the test tube or cuvette to be regulated. When a plurality of the above-mentioned bodies have been attached by a stem to the carrier plate with a given spacing, the moving of a plurality of the bodies mentioned becomes very easy. The carrier plate may be transparent, or it has apertures for the measuring beams when the measurements are made according to the vertical measurement principle or when the carrier plate is used in conjunction with receptacle plates.

The ring of the invention may also be used in sampling and in analyses, e.g., as follows:

1. A ring made of a suitable material has been coated with a given antigen.

2. The ring is pushed to reside, e.g., on the nasal or pharyngeal mucosa, from which the antigens on the ring will pick up antibodies corresponding thereto.

3. The ring is washed with a suitable washing solution in such a manner that the antibodies present on the mucosa, if any, are not detached from the ring.

4. The assay may continue by conventional means used in EIA methods. The ring is placed in a test tube, a cuvette, a cuvette element, or in the depression of a receptacle plate and the reaction mixture is added, which usually contains a buffer and the antibody enzyme conjugate corresponding to the antibody that is being determined. The reaction mixture containing substrate is added after incubation and washing. The result is judged by the colour produced, or a more precise either kinetic or end-point measurement is performed.

Using the procedure just described, it is possible to make a rapid diagnosis, e.g., of respiratory tract or urinary tract infections. It is furthermore an easy thing to store and to transport the sample of the ring.

The ring onto which a sample is taken, e.g., in the manner described may also be used for the determination itself. The conditions are arranged, either on the ring itself or by adding one or several reagents or by intermediate steps in which one or several reagents are washed off, to be such that the fixation on the ring of the substance that is being measured causes, e.g., a visually observable colour reaction, or it is possible from the strip or ring to wash the colour, e.g., into a test tube and subsequent to such washing by adding one or several reagents to make the colour visible.

The sample may also be taken onto a strip, treated in various ways and having various shapes, which may be bent to form an open or closed circular ring. Such a bent ring may be placed, e.g., in a test tube, a cuvette, a cuvette element or the depression of a receptacle plate.

The strip just described may also have various extensions by which the strip can be held. After the sampling and transfer operations and extension may, if required, be detached from the strip proper or it may follow along in the analysis. It is obvious that the strip itself or its extensions may carry markings for the strip's identification. Such markings may be either written or pre-printed. The identification of the strip may be read both visually and electrically. It goes without saying that in the indentification marking and in its reading operation all and any techniques known in the art may be used.

Likewise, for the identification of all of the exemplifying embodiments described above, it is possible to use all known techniques.

In the following, a few exemplifying embodiments of the invention are illustrated by schematic diagrams.

In FIG. 1 a ring is shown. The size and material of this ring may vary in the ways presented above and hereinafter. The ring may be either closed or open.

Figure 2:
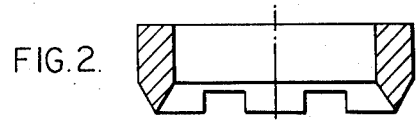

FIG. 2 shows the ring in cylindrical shape. It is obvious that the cylinder may have different shapes, the surfaces may either be smooth or they may present various configurations. The outer surface may also be conical or straight, and so may the inner surface.

Figure 3:
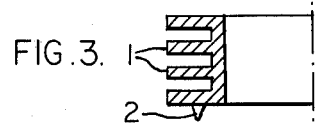

FIG. 3 shows, as an exemplifying embodiment, a ring which is cylindrical and whose outer surface area has been extended by the projections 1, and an eminence 2 runs underneath the lower part of the ring. The eminence 2 may be continuous or discontinuous. The sharp-edged eminence 2 prevents the lower edge of the ring from resting, e.g., against the bottom of a level bottom cuvette.

Figure 4:
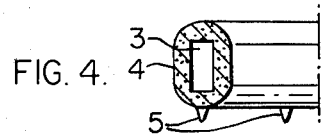

The ring in FIG. 4 has a core portion 3 and a mantle portion 4, and eminences 5, of which there may be three or more on the lower surface of the ring. The core part 3 and mantle part 4 may have the same or different materials. The core part 3 may, for instance, serve as mechanical support and the mantle part 4 as binder of a given substance or substances. The core part 3 may consist of iron, in which case it is possible to use a magnet to remove the ring from the test tube, cuvette or receptacle plate depression.

Figure 5:
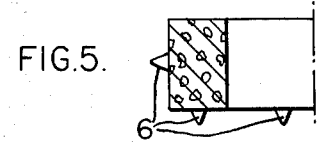

FIG. 5 shows a ring, shown to be porous, whereby the surface area increases. The ring also has eminences 6 on the outer as well as lower face. Said eminences may be part of a ring of any conceivable shape and made of any conceivable material.

Figure 6:
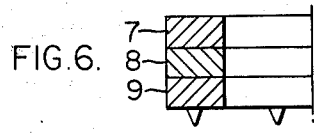

FIG. 6 shows a ring consisting of three different layers 7, 8 and 9. The layers may be of one material or of different materials. They may be provided in any number and they may have any conceivable shape and any conceivable succession.

Figure 7:
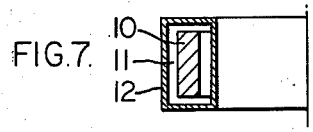

The ring in FIG. 7 has a core part 10, a middle part 11, and a mantle part 12. The number of layers is arbitrary, and the thickness and configuration of the layers may vary. The functions of the different layers are variable. For instance, the core part 10 may bind the enzyme and the mantle part 12 passes through only molecules which are smaller than the enzyme concerned. The ring may then operate, e.e., as an enzyme electrode, as was described earlier.

The rings described above may be constructed, e.g., so that they mate either with a small free play or solidly, by mediation of the outer surface of the ring or its eminences or other equivalent projections, with the wall of the cuvette, test tube or receptacle plate. The wall of the cuvette, test tube or receptacle plate may also have, e.g., an eminence, a projection, rib or equivalent by means of which the ring abuts on the wall either solidly or with a small free play.

Figure 8:
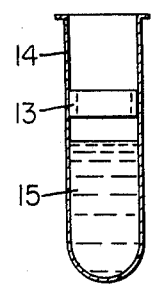

In FIG. 8 a ring 13 is depicted which resides at a desired height, e.g., in a test tube 14. When the test tube is shaken, for instance during the incubation, the liquid 15 in the test tube will rise to the height of the ring 13 and, if required, slightly above it. The ring 13 is then in contact with the liquid 15 only during such shaking and the substance or substances of the ring may react with the substance in the liquid. Agitation adds to the speed of the reaction.

Figure 9:
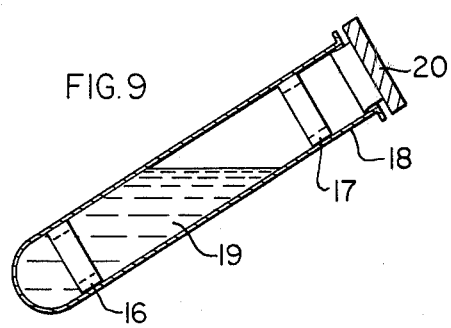

In FIG. 9 two similar or dissimilar rings 16 and 17 are disposed in one test tube 18. The substances in the liquid 19 may react, for instance, first with the substances of ring 16 and thereafter with those of ring 17, if the test tube 18 is inverted. If the test tube 18 is shaken, the substances of the liquid 19 therein will react with the substances of both ring 16 and ring 17. It is obvious that there may be one or several rings, anchored in this manner at desired height to the wall of the test tube. Furthermore, one or several reacting substances may be affixed to the stopper 20 of the test tube. The test tube may be replaced by a cuvette, a cuvette element, a depression of a receptacle plate, or any other reaction vessel. In the foregoing, when reference has been made to a cuvette or a test tube, and subsequently when such reference is made, the same may apply equally to any conceivable reaction vessel, tube, container or reaction space.

Figure 10:
Figure 11:
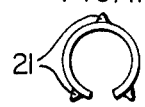

In FIG. 10 an open ring is seen in elevational view, and the same ring is shown in top view in FIG. 11. A ring of this type can have any conceivable shape, for instance that of any one of the rings already described, and the extent of the open portion may vary. A ring of this type may also have different layers as well as eminences 21 on its outer or lower surface. In addition, a ring of this type may also be formed of the above-mentioned strip of varying shape and it is used as was already described. An open ring of this type may be disposed in the test tube either loosely or solidly, as was described in the foregoing.

Figure 12:
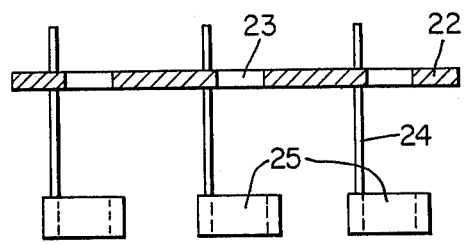

FIG. 12 displays a supporting plate 22 with holes 23 for the measuring beams, and carrying rings 25 on extensions 24. As was described above, the position of the rings with respect to the supporting plate 22 may be regulated with the aid of the extensions 24. The use of this embodiment has been described earlier.

Figure 13:
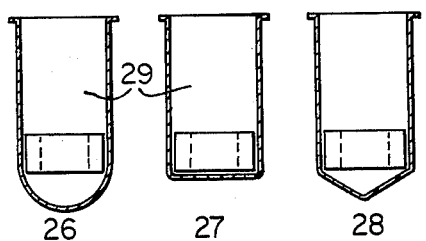

FIG. 13 depicts depressions or tubes 26, 27 and 28 with U-shaped, level or V-shaped bottom. In the depressions, rings 29 have been placed. When the cuvette is measured in vertical direction (light passing vertically, in the direction of the longitudinal axis of the cuvette) the ring 29 within the cuvette is in the horizontal position shown in FIG. 13, whereby the light can pass through the central aperture of the ring. When the measurement is carried out according to the traditional horizontal measuring principle (the light running in the horizontal plane, first through one vertical wall of the cuvette, next through the liquid column and finally through the outer, vertical wall of the cuvette), the ring is placed in vertical position in the cuvette, whereby the light may pass through the central ring aperture. When measuring according to the vertical or horizontal measuring principle, the ring may be circular, square, rectangular, or of any other shape. In this connection the ring may also be open as is shown in FIGS. 10 and 11. Conforming to the principles described above, the ring may also be used in a centrifugal analyzer wherein the light runs vertically: first through one cuvette wall, next through the liquid column and last through the second cuvette wall to the detector. In a centrifugal analyzer the ring is placed in a horizontal plane. Here, as in all the preceding embodiments, the ring may have any conceivable shape (e.g., ring, cylinder, square, rectangle, conical cylinder), it may consist of various materials and it may be coated in various ways and be either solid or open. The ring may also be cubic, having in opposed faces apertures for passage of the light measurement beam, or it is a massive body of any conceivable shape having an aperture through which the measurement beam may pass. The right just mentioned above and those described before may be placed singly in the cuvette or test tubes or several may be placed at once, utilizing supporting plates (cf. the description associated with FIG. 12, for instance), in the test tubes of a test tube element, in the depressions of a receptacle plate, in the cuvettes of a cuvette element, or in separate test tubes or cuvettes in a matrix.

The extensions 24 of the supporting plate 22 depicted in FIG. 12 may be, e.g., magnetic or magnetizable, whereby, if the rings 25 contain iron, the rings become adherent to the extensions 24. The rings 25 may be disposed in the horizontal or vertical plane, depending on the direction of the measuring beam. Here, too, the rings may have any conceivable shape. They may moreover be, e.g., closed or open rings (as was described above) which are, e.g., circular, square, rectangular, or have the shape of any other polygon. An iron part in a separate ring also enables, e.g., a ring within the test tube or cuvette to be rotated from outside the test tube with the aid of a magnetic stirrer. Hereby an efficient agitation is obtained, e.g., for the duration of the reaction within the test tube.

Figure 14:
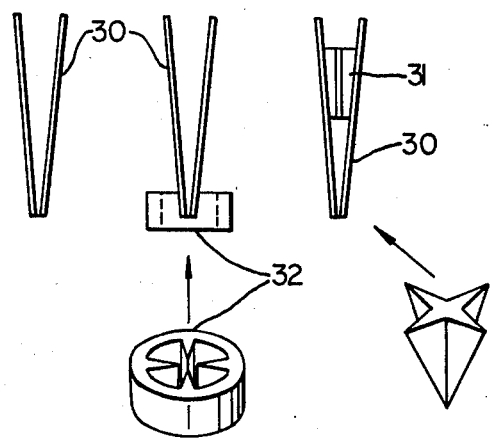

In FIG. 14 tips 30 of pipettes are seen, which are separate or are parts of a tip plate element. Within each tip 30, a conical ring 31 can be placed, whereby, within the pipette tip, a reaction may take place. Here, too, the rings may be applied in different modifications and in different ways, as was described above. It is possible to place a ring 32 on the outside of the tip 30, and this is used in the manner already described. The tip plate may also conveniently be used for transportation of the rings 32 if the ring 32 has a suitable position which can be engaged with the tip 30. One or several rings may be disposed within or outside the tip. It is, of course, also possible to use the tips on the plate as rings, with the treatments, materials and procedures described above.

Figure 15:
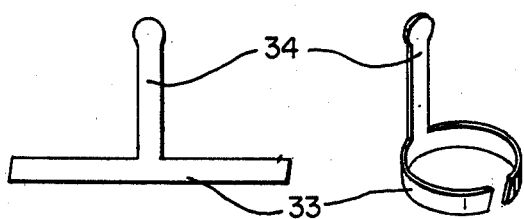

In FIG. 15, an example is presented of a strip 33 and of the extension 34 thereon. The extension 34 may connect with the strip 33 in different ways, and it may be permanently integral therewith or detachable. Furthermore the strip may also be without extension. The construction and use of the strip were described earlier.

What we claim is:

1. A form piece mountable within a laboratory test vessel and adapted to be coated with and hold on at least a portion of its surface a material useful in laboratory tests includes:
   a ring-like body member having an aperture extending there through and an outer surface; and
   at least one projecting member extending outwardly from the outer surface area of said body member to space the body member from the vessel.

2. A form piece as claimed in claim 1 in which said body member is a hollow cylindrical member and said at least one projecting member extends outwardly from one of the lateral portions of said outer surface of said cylindrical member to space said body portion from the bottom of said vessel.

3. A form piece as claimed in claim 2 including at least one lateral projecting member extending outwardly from the longitudinal surface of said body member to space said body portion from the side of said vessel.

4. A form piece as claimed in claim 3 including a plurality of said lateral projecting members spaced a predetermined distance apart along the longitudinal side of said body member, each of said lateral projecting members being continuous rings defining grooves in the longitudinal of the body.

5. A form piece as claimed in claim 1 in which at least a portion of said body member is made of a porous material.

6. A form piece as claimed in claim 1 in which said body member includes a central core of a magnetic material and a layer of non-magnetic material surrounding said core.

7. A form piece as claimed in claim 1 in which said body member comprises a laminate of at least two different materials.

8. A form piece as claimed in claim 1 including an elongated member attached to said body member to act as a handle.

* * * * *